United States Patent
Goudaliez et al.

(10) Patent No.: US 7,621,298 B2
(45) Date of Patent: Nov. 24, 2009

(54) RECIPIENT EQUIPPED WITH AN ASEPTIC TRANSFER SYSTEM

(75) Inventors: Francis Goudaliez, Faches-Tumesnil (FR); Thierry Verpoort, Halluin (FR)

(73) Assignee: Maco Pharma, S.A., Mouvaux (FR)

( * ) Notice: Subject to any disclaimer, the term of this patent is extended or adjusted under 35 U.S.C. 154(b) by 10 days.

(21) Appl. No.: 11/977,354

(22) Filed: Oct. 24, 2007

(65) Prior Publication Data
US 2008/0128046 A1    Jun. 5, 2008

(30) Foreign Application Priority Data
Oct. 31, 2006    (FR)    ................................ 06 09571

(51) Int. Cl.
- B65B 3/04    (2006.01)
- A61B 19/02    (2006.01)
- A61J 1/05    (2006.01)

(52) U.S. Cl. .................. 141/5; 141/114; 141/311 R; 141/369; 604/403; 604/406; 604/414; 220/729; 220/744

(58) Field of Classification Search .............. 141/1, 141/5, 10, 114, 311 R, 312, 319–323, 369; 141/382; 604/403, 406, 408, 414; 53/425–426; 220/375, 729, 744; 222/206, 209, 211–213
See application file for complete search history.

(56) References Cited

U.S. PATENT DOCUMENTS

| | | | |
|---|---|---|---|
| 983,348 A * | 2/1911 | Carpenter | 222/209 |
| 3,125,092 A * | 3/1964 | Cohen | 604/414 |
| 4,253,500 A * | 3/1981 | Williams | 141/1 |
| 4,347,874 A * | 9/1982 | Sullivan et al. | 141/1 |
| 4,413,990 A * | 11/1983 | Mittleman | 604/122 |
| 4,610,670 A | 9/1986 | Spencer | |
| 4,737,214 A | 4/1988 | Leurink et al. | |
| 6,357,488 B1 * | 3/2002 | Brossard et al. | 141/1 |

FOREIGN PATENT DOCUMENTS

| | | |
|---|---|---|
| EP | 0 044 204 | 1/1982 |
| EP | 0 526 678 | 2/1993 |
| EP | 0 548 577 | 6/1993 |
| EP | 0 756 121 | 1/1997 |
| EP | 1 034 772 | 9/2000 |

* cited by examiner

*Primary Examiner*—Timothy L Maust
*Assistant Examiner*—Nicolas A Arnett
(74) *Attorney, Agent, or Firm*—Bachman & LaPointe, P.C.

(57) ABSTRACT

A recipient has a body designed to contain a fluid and an orifice by which the fluid may be introduced into the body. The recipient is equipped with a system for the sterile transfer of the fluid from inside the body. The transfer system comprises a deformable and impervious wall, wherein the wall is positioned with respect to the recipient so that it forms a closed and sterile space inside which the orifice is located, a fluid communication device between the closed space and the outside of the recipient, wherein the device may be handled without compromising the sterility, and a seal structure associated with the orifice, wherein the seal structure is at least partially located inside the closed space so that it may be moved between an open position and a closed position of the orifice.

17 Claims, 4 Drawing Sheets

RECIPIENT EQUIPPED WITH AN ASEPTIC TRANSFER SYSTEM

BACKGROUND (1) Field of the Invention

The invention relates to a recipient designed to contain a fluid, wherein said recipient is equipped with a sterile transfer system for the fluid inside said recipient. The invention also relates to an aseptic transfer process of a fluid from a first recipient to another recipient of the invention.

It typically applies to the case where the first recipient is a flexible bag containing a medical fluid and the recipient of the invention is a rigid jar.

(2) Prior Art

In the field of blood transfusions, classically the blood is taken and its constituents such as plasma and the red blood cell concentrates are separated into bag systems such as those described in the document EP-A1-526678. These systems, called closed, permit the sterility of the separated blood constituents to be guaranteed.

Once they are separated into different bags, the blood cell constituents may undergo different treatments such as filtration, bacterial and/or viral decontamination or freeze drying.

However, certain treatments may not be carried out in the bags of the closed system used to sample or separate the blood cell constituents. For example, certain treatments require the blood cell constituents to be transferred to rigid jars, especially made of glass.

There are many types of transfer devices in the medical field, especially for the medicinal reconstitution of a medication contained in a glass jar to an infusion bag. Such a device is described for example in the document EP-A1-1034772. However, this type of device does not permit the aseptic transfer of fluid between a bag and a jar.

The document EP-A1-0548577 describes a stopper for a jar comprising a sealed tube designed to make a sterile connection with another sealed tube, for example that of an infusion bag or a syringe. This specific stopper permits the transfer of the fluid contained in the jar to be made to the jar or syringe in a sealed in a closed system.

This set up requires a specific stopper to be made which, apart from the cost, is a constraint for subsequent handling of the sealed jar. Furthermore, the stopper function may be damaged when the tube is passed through it.

SUMMARY OF THE INVENTION

The invention aims to resolve the problems of the prior art by providing in particular a recipient equipped with a system for sterile transfer which does not require a specific stopper to be made and which permits the recipient to be used as usual after the transfer.

To this end, and in one first aspect, the invention proposes a recipient comprising a body designed to contain a fluid and an orifice through which said fluid may be introduced into said body, wherein said recipient is equipped with a sterile transfer system for the fluid inside said body, wherein said recipient is characterised in that said transfer system comprises:
- a deformable and impervious wall, wherein said wall is located with respect to the recipient so that it forms a closed and sterile space in which the orifice is located;
- a device for communication of fluids between the closed space and the outside of the recipient, wherein said device may be moved without compromising the sterility;
- a sealing means for the orifice, wherein said means is at least partially located in the closed space so that it may be moved between an open position and a closed position of the orifice.

In one second aspect, the invention relates to an aseptic transfer process for a fluid from a first recipient to another recipient in the first aspect, wherein said process comprises the steps which include:
- creating the communication between the two recipients by sterile handling of the fluid communication device;
- transferring the fluid from the first recipient to the body of the second recipient;
- actuating the sealing means from their open position to their closed position by deformation of the wall.

BRIEF DESCRIPTION OF THE DRAWINGS

Other purposes and advantages will become clearer in the following description in reference to the appended drawings.

DETAILED DESCRIPTION OF THE PREFERRED EMBODIMENT(S)

In the following description, the terms upstream and downstream are defined with respect to the direction of the flow of the fluid during the aseptic transfer, which is to say from the first recipient to another recipient of the invention.

Figure 1:
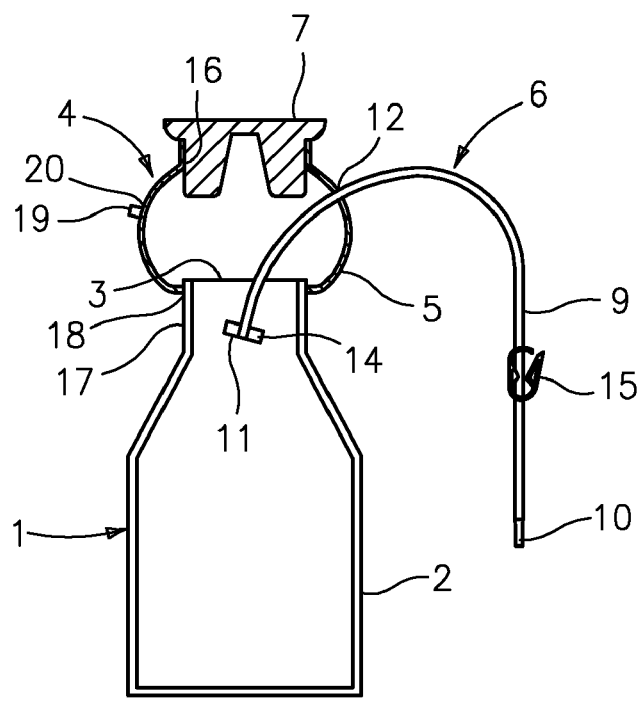
FIGS. 1 and 6 show a diagrammatical front view face of a recipient in two different embodiments of the invention.
Figure 6:
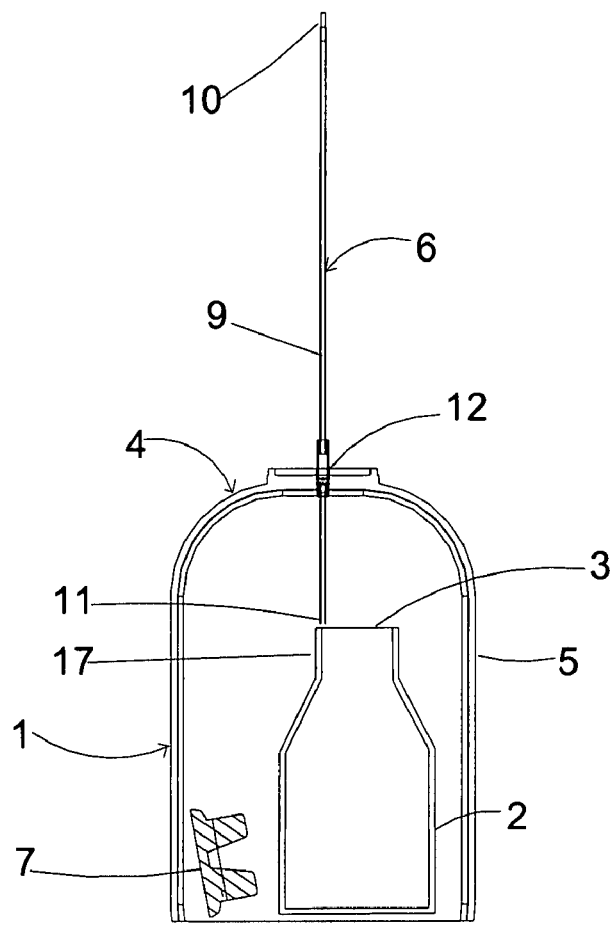

In FIG. 1 or 6, the recipient 1 of the first aspect of the invention comprises a body 2 designed to contain a fluid and an orifice 3 through which said fluid may be introduced into said body 2.

The recipient is made from a flexible or a rigid material, that may be sterilised in particular by steam, ethylene oxide, gamma radiation or beta radiation. In particular, the recipient is a glass jar or bottle.

The recipient 1 is equipped with a system 4 for the sterile transfer of the fluid inside said body 2, wherein said transfer system comprises:
- wall 5 that is deformable and impervious, wherein said wall is located with respect to the recipient 1 so that it forms a closed and sterile space in which the orifice 3 is located;
- device 6 for the communication of fluids between the closed space and the outside of the recipient, wherein said device may be moved without compromising the sterility;
- means 7 of sealing the orifice, wherein said means 7 is at least partially located in the closed space so that it may be moved between an open position and a closed position of the orifice 3.

This transfer system 4 permits the sterile transfer of a fluid contained in a first recipient to the recipient 1, which is to say the transfer of the fluid without bringing the fluid into contact with the ambient air and the possible contaminants that may be present in the ambient air.

The system 4 comprises a wall 5 that is deformable and impervious forming a closed and sterile space in which the orifice 3 of the recipient is located. Consequently, the inside of the recipient is also sterile.

The sterility of the closed space is obtained during the manufacture of the recipient, by sterilisation of the recipient equipped with the transfer system. The method of sterilisation depends on the materials used to make the various components of the recipient.

The wall 5 of the transfer system 4 is deformable so that it is possible to move the constituents in the closed space manually and from the outside, and especially the means 7 of sealing the orifice.

The wall 5 is impervious to preserve the sterility of the recipient and the closed space formed by the wall.

In one specific embodiment, the wall is flexible and made from a polymer material, especially, from a material that may be sterilised using one of the methods mentioned above, for example on polyvinyl chloride or silicon. The choice of the material depends on its resistance to sterilisation and its mechanical properties.

Figure 5:
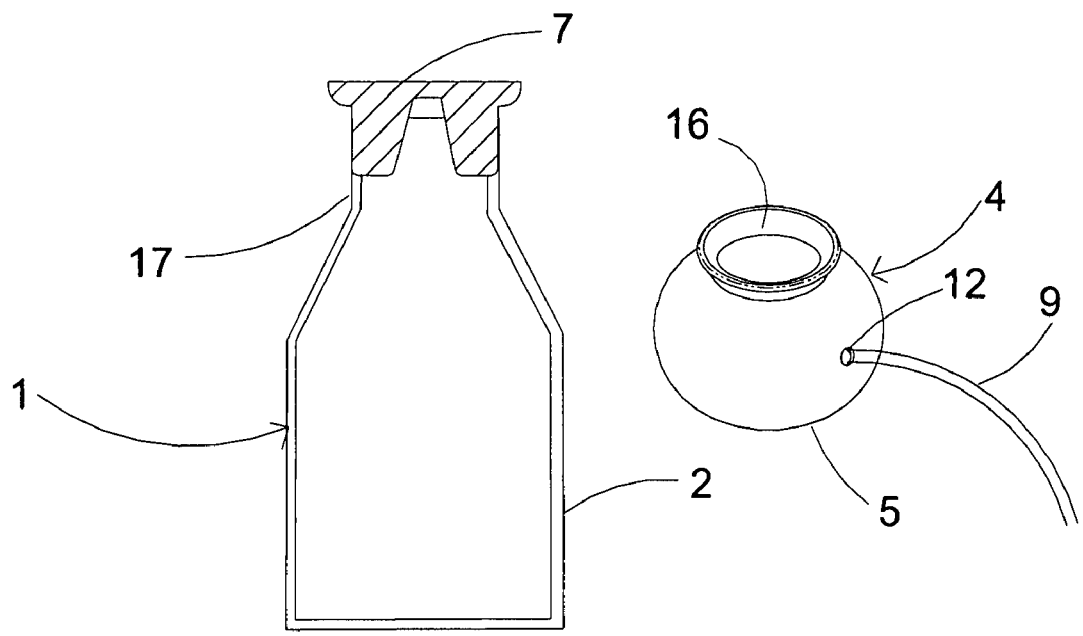

In FIG. 1 or 5, the wall 5 has the form of a flexible sleeve, of which one end is assembled around the orifice 3 of the recipient and the other end around the sealing means 7. The sleeve is for example injection moulded.

In FIG. 6, the wall 5 is formed by two flexible sheets assembled at their edges to form an envelope.

In another embodiment (not shown), the wall 5 is rigid or semi rigid and has gussets or folds which make the wall flexible.

The system further comprises a device 6 for the communication of fluids between the closed space and the outside of the recipient. This communication device 6 may be moved without compromising the sterility, which is to say that when it is actuated, it does not impair the sterility of the recipient.

Figure 2:
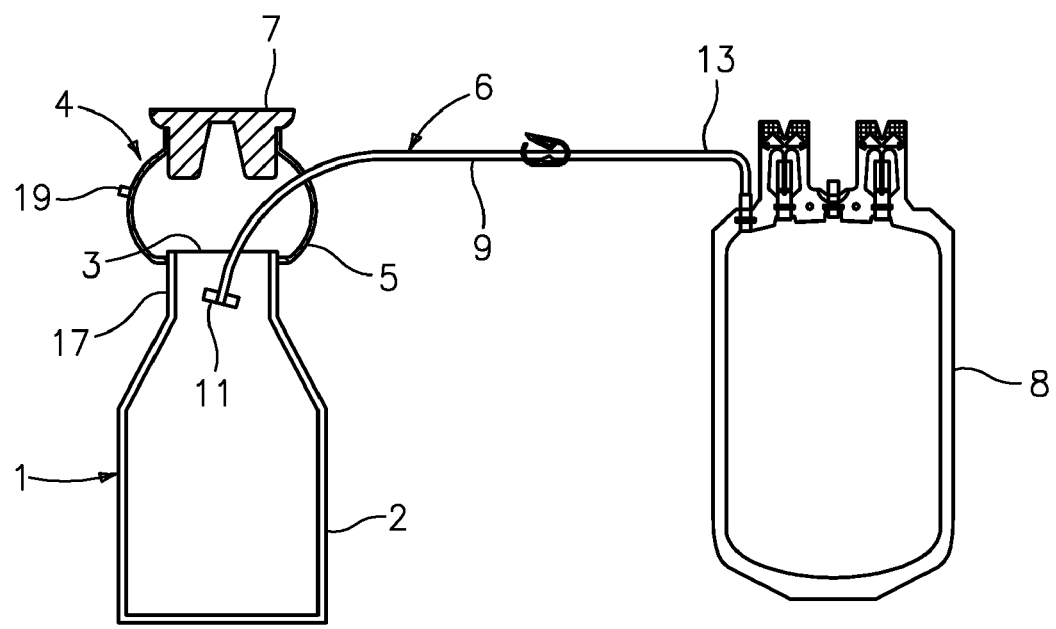
FIGS. 2 to 5 show diagrammatically the steps of the process of the invention of the aseptic transfer from a bag to the recipient of FIG. 1.

In relation with FIG. 2, the fluid communication device 6 is designed to permit the transfer of a fluid contained in a first recipient 8 located outside the recipient 1 of the invention to the inside of said recipient 1.

This transfer is aseptic, so as to avoid contaminating the fluid with contaminants from the ambient air.

In one specific embodiment shown in FIG. 1 or 6, the fluid communication device 6 comprises a flexible tube 9 traversing the wall 5, wherein the upstream end 10 of said tube is located outside of the closed space and the downstream end 11 is located inside said space.

To this end, the wall 5 comprises a first orifice 12 whose diameter is substantially equal to the diameter of the flexible tube 9 to ensure the impervious seal of the wall 5. To improve this impervious seal, the orifice 12 is equipped for example with an elastomer ring.

In FIGS. 1 to 6, the upstream end 10 of the tube is closed and the downstream end 11 of the tube is open.

The tube 9 is made from a material that is divisible and that may be welded, such as polyvinyl chloride. It is therefore possible to make a sterile connection with another closed tube 13 fitted onto a first recipient 8 using a sterile connection apparatus. Such apparatus is available on the market and includes the SCD® 312 manufactured by Terumo.

The sterile connection process used by this apparatus is described for example, in the documents EP-044 204, EP-0 134 630 and EP-0 208 004.

In one variant that is not shown, the upstream end 10 of the tube 9 is equipped with a connector that may be used to make a sterile connection with another connector connected to a first recipient 8 containing a fluid. Such connectors are for example described in the document EP-0 756 121.

In these two variants, the connection between the recipient 1 of the invention and the first recipient 8 containing the fluid must be sterile, which is to say that the fluid must not be able to brought into contact with the contaminants of the ambient air.

This recipient therefore permits a sterile connection to be made between a first recipient 8 containing a fluid, such as a bag, and a recipient 1 such as a jar or a glass bottle. This recipient equipped with a transfer system 4 avoids the pre-connection of the first recipient 8 during manufacture. There is no need either for later sterilisation of the connection between the two recipients 1, 8 or of the fluid.

To make handling the recipient easier, the tube 9 is mounted so that it may slide imperviously through the wall 5. Consequently, the tube 9 may be initially introduced into the body 2 of the recipient 1, and after the transfer of the fluid, removed by traction to allow the sealing means 7 to be fitted.

To avoid breaking the sterility of the closed space by penetrating part of the tube, that was initially outside the recipient and therefore potentially contaminated, into the closed space, the tube 9 slides towards the outside of the closed space and is prevented from sliding towards the inside.

To this end, the tube 9 is for example, equipped with locking means, such as grooves.

The part of the tube located in the closed space is equipped with means forming a stop 14 when the tube slides through the wall.

In the figure, the means forming a stop is a stop positioned at the downstream end 11 of the tube, preventing the tube 9 from being removed completely from the closed space. Consequently, the sterility of the closed space is preserved.

To control the flow of the fluid in the tube, it is equipped with means 15 of controlling the flow in the tube such as a clamp or a circuit valve.

Figure 7:
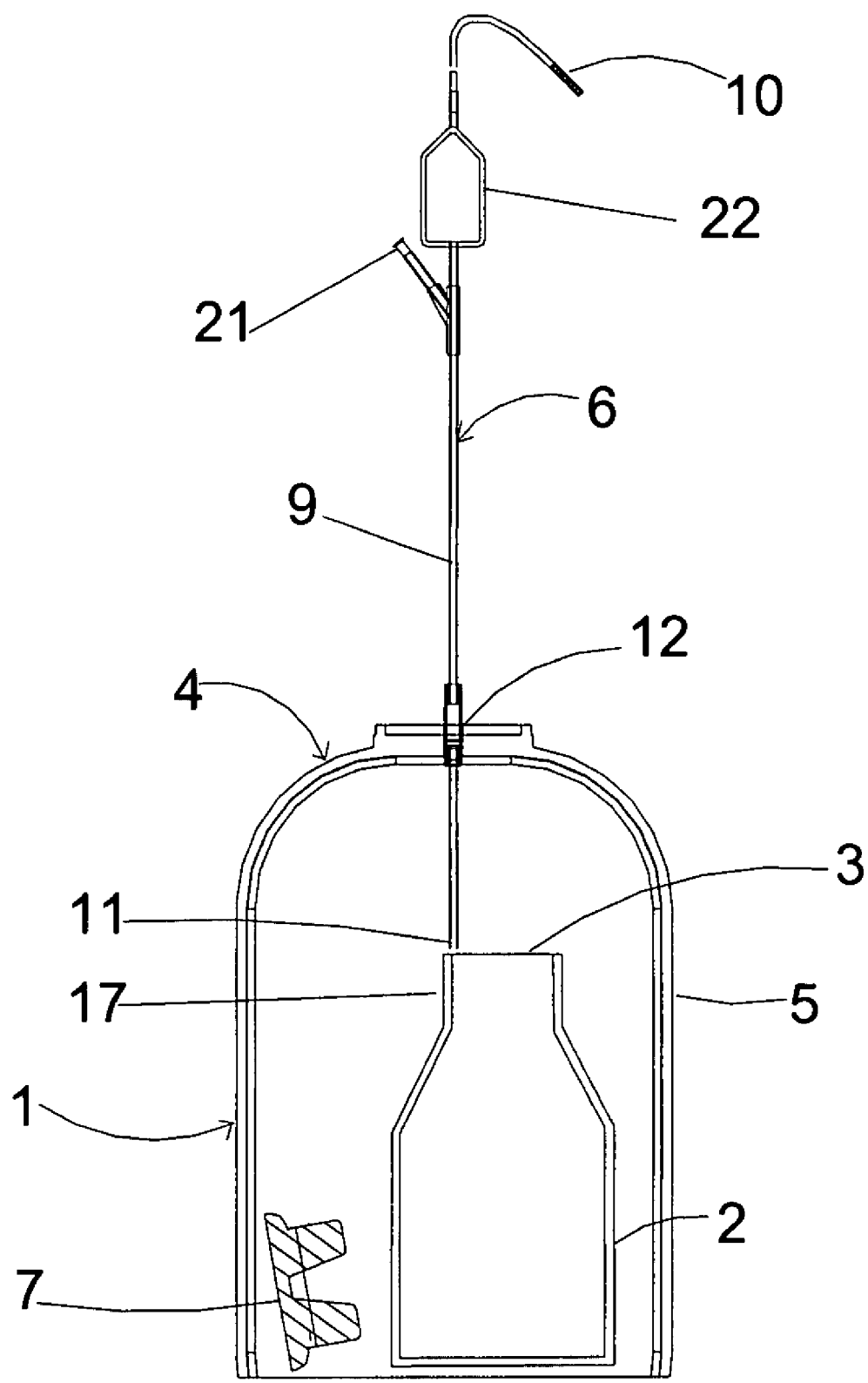
FIG. 7 shows one variant of the embodiment of the recipient of FIG. 6.

In one variant shown in FIG. 7, the flexible tube comprises ventilation means 21 such as an air inlet or a vent. The ventilation means 21 are capable of letting gases pass. The ventilation means 21 are for example positioned on a tube connected to the tube 9 traversing the wall of the transfer system 4.

The ventilation means 21 are selected so that they do not compromise the sterility of the recipient 1. For example, the air inlet or vent has a membrane with a pore size that is small enough to prevent bacteria from passing into said recipient. The size of the pores is in particular smaller than or equal to approximately 0.22 µm.

These ventilation means 21 are used in the manufacture of the recipient and in particular during the sterilisation of the recipient 1 equipped with the transfer system.

In fact, during sterilisation by steam, the transfer system swells due to the effect of the expansion of the air in the system. This excess pressure creates a risk of the transfer system 4 bursting. The ventilation means 21 permit this excess pressure to be avoided by allowing part of the air to be purged from the system.

In another variant shown in FIG. 7, the tube 9 is equipped with means for filtering the fluid designed to be contained in the recipient 1. The filtration means are notably in the form of a filtration device 22 capable of eliminating the pathogens from the fluid.

In the case where the fluid is plasma, the filtration device comprises for example a membrane with a pore size of less than 0.22 µm so as to eliminate any bacteria contained in the plasma.

This filtration device ensures that the fluid transferred into the recipient does not contain pathogens and especially no bacteria.

In another variant not shown, the filtration means 22 also act as the ventilation means. In this case, the downstream end 11 of the tube is not closed. The filtration/ventilation means are capable of letting the gas and the fluids pass.

The transfer system 4 finally comprises sealing means 7 that may be moved between an open position (FIG. 1) and a closed position (FIG. 4) of the orifice of the recipient 1.

In one embodiment, the sealing means 7 are in the form of a stopper which may be inserted into the orifice 3 of the recipient 1 to seal it.

In one variant, the sealing means 7 may be screwed or clipped onto the orifice 3.

In FIG. 1, the sealing means 7 traverse the wall 5 and are opposite the orifice 3, wherein said sealing means are mounted imperviously on the wall 5.

To this end, the wall 5 comprises a second orifice 16 in which the sealing means 7 are located. As the first orifice 12, the second orifice 16 may comprise a sealing ring.

In particular, the sealing means 7 comprise a body whose lower section is formed so that it may be introduced into the orifice so that an impervious seal may be formed, wherein said lower section is located in the closed space.

In FIG. 1, the upper section of the body of the sealing means 7 is located outside of the closed space.

Consequently, to seal the recipient 1 of the invention, the upper section of the body of the sealing means 7 is pressed, to introduce the lower section into the orifice 3 of the recipient. The deformable wall makes this operation possible.

In relation to FIGS. 1 to 5 and in one first variant, the orifice 3 of the recipient is fitted onto a neck 17, wherein the wall 5 is fitted imperviously around said neck 17.

To this end, the wall 5 is equipped with a third orifice 18 in which the neck 17 of the recipient 1 is located. Advantageously, this orifice 18 is equipped with a sealing ring.

In another variant shown in FIG. 6, the wall is positioned around the recipient 1 assembly so that said recipient is contained inside the closed space.

To facilitate the manufacture of the wall 5, the sealing means 7 are contained inside the closed space, only the tube 9 forming the fluid communication device 6 traverses the wall 5.

In particular, the wall 5 has the form of a gloves equipped with at least two fingers to facilitate the handling of the recipient 1 and the sealing means 7 outside of the recipient.

Advantageously, the wall is equipped with an air inlet 19. The air inlet 19 is located in a fourth orifice 20 of the wall 5. This air inlet 19 permits the recipient 1, which is especially rigid, to be filled, by driving out the air from the closed space to the outside of the recipient 1.

In one second aspect, the invention relates to an aseptic transfer process for a fluid from a first recipient 8 to a recipient 1 of the first aspect of the invention, wherein said process comprises the steps which include:

creating the communication between the two recipients 1, 8 by sterile handling of the fluid communication device;
transferring the fluid from the first recipient 8 to the body of the recipient 1 of the invention;
actuating the sealing means 7 from its open position to its closed position by deformation of the wall 5.

This process applies especially to the case of a sterile transfer of fluid contained in a first recipient 8 such as a flexible bag, to a rigid recipient 1 such as a glass jar or bottle.

In FIGS. 1 to 7, when the recipient 1 is equipped with a tube 9, the communication is created by means of a sterile connection between the tube 9 and a closed tube 13, that is divisible and may be welded on the first recipient 8 so that the communication is created with the fluid contained inside said recipient 8.

In the case of the recipient of FIG. 1, before or after the sterile connection, the downstream end 11 of the tube 9 is located inside the body 2 of the recipient 1 to allow the fluid to be introduced inside said recipient (FIG. 2).

Figure 3:
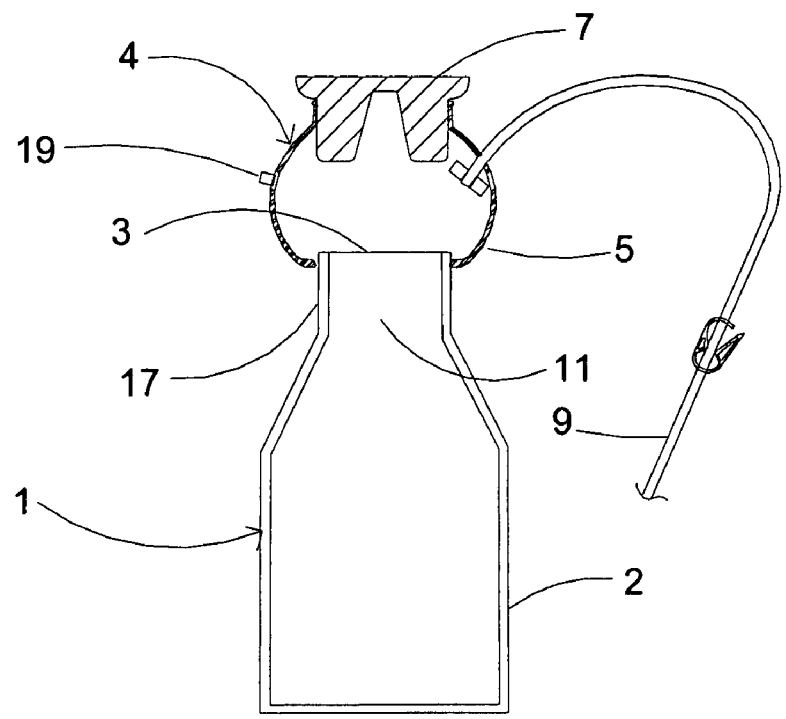

After the transfer of the fluid, the tube 9 is removed from inside the body 2 of the recipient by pulling it out, whilst maintaining its downstream end 11 inside the closed space (FIG. 3). This operation is secured by means of a stop 14 on the downstream end 11 of the tube 9.

Figure 4:
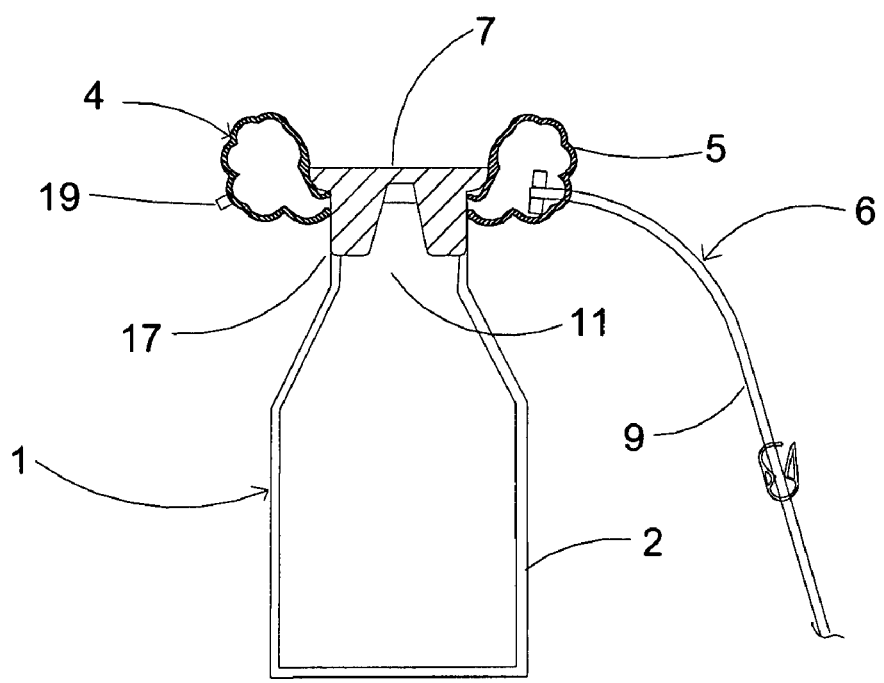

In FIG. 4, to seal the body of the recipient, pressure is exerted on the sealing means 7 so that it is introduced into the neck of the recipient.

Once the recipient has been sealed, the inside of the body of the recipient 1 is sealed and sterile. If the wall 5 is sufficiently flexible and elastic, it may be removed from the neck 17 of the recipient, leaving the recipient sealed from the ambient air (FIG. 5). The inside of the recipient has not at any time been brought into contact with the contaminants of the ambient air, and so the transfer is aseptic.

In FIG. 6, when the recipient 1 and the sealing means 7 are contained inside the closed space, the transfer process is carried out as follows.

Before or after the sterile connection, the sealing means 7 are removed from the neck of the jar 7 by handling outside of the wall 5.

The tube 9 is introduced into the neck of the recipient 1 and the fluid transfer is carried out. At the end of the transfer, the sealing means 7 are placed on the neck of the jar to seal it.

The wall 5 is then opened, for example by cutting it open, to recover the sealed recipient containing the fluid.

The sealed recipient containing the fluid is then used as usual to undergo subsequent treatments, such as for example the freeze drying of the fluid contained inside.

What is claimed is:

1. A recipient comprising a body designed to contain a fluid including an orifice by which said fluid may be introduced into said body, a system for sterile transfer of the fluid inside said body, said transfer system comprising a deformable and impervious wall positioned with respect to the recipient so that said wall forms a closed and sterile space inside which the orifice is located, a fluid communication device between the closed space and an outside of the recipient which can be handled without compromising sterility, and sealing means for the orifice, said sealing means being at least partially located inside the closed space so that the sealing means may be moved between an open position and a closed position of the orifice.

2. The recipient according to claim 1, wherein the wall is made of a polymer material.

3. The recipient according to claim 1, wherein said recipient is made of a rigid material.

4. The recipient according to claim 1, wherein the fluid communication device comprises a flexible tube traversing the wall, and wherein an upstream end of said tube is located outside the closed space and a downstream end is located inside said closed space.

5. The recipient according to claim 4, wherein the flexible tube comprises ventilation means for the transfer system.

6. The recipient according to claim 4, wherein the flexible tube is equipped with means for filtering pathogens from the fluid intended to be contained in the recipient.

7. The recipient according to claim 4, wherein the upstream end of the tube is sealed and the downstream end of the tube is open.

8. The recipient according to claim 4, wherein the tube is made from a divisible material that may be welded.

9. The recipient according to claim 4, wherein the tube is mounted to slide imperviously through the wall.

10. The recipient according to claim 1, wherein the sealing means traverses the wall and is opposite the orifice and wherein said sealing means are mounted imperviously on the wall.

11. The recipient according to claim 10, wherein the sealing means comprise a body whose lower section is formed to be introduced into the orifice so that the orifice may be sealed imperviously and wherein said lower section is located inside the closed space.

12. The recipient according to claim 1, wherein the orifice is fitted on a neck and wherein the wall is positioned imperviously around said neck.

13. The recipient according to claim 1, wherein the wall is positioned entirely around the recipient so that said recipient is contained inside the closed space.

14. The recipient according to claim 1, wherein the wall is equipped with an air inlet.

15. A recipient comprising a body designed to contain a fluid including an orifice by which said fluid may be introduced into said body, a system for sterile transfer of the fluid inside said body, said transfer system comprising a deformable and impervious wall positioned with respect to the recipient so that said wall forms a closed and sterile space inside which the orifice is located, a fluid communication device between the closed space and an outside of the recipient which can be handled without compromising sterility, and sealing means for the orifice, said sealing means being at least partially located inside the closed space so that the sealing means may be moved between an open position and a closed position of the orifice, wherein the fluid communication device comprises a flexible tube traversing the wall, and wherein an upstream end of said tube is located outside the closed space and a downstream end is located inside said closed space, wherein the tube is mounted to slide imperviously through the wall, and wherein a section of the tube located inside the closed space is equipped with means for forming a stop when the tube slides through the wall.

16. An aseptic transfer process for a fluid from a first recipient to a second recipient wherein said process comprises the steps of:
   providing said second recipient comprising a body designed to contain a fluid including an orifice by which said fluid may be introduced into said body, a system for sterile transfer of the fluid inside said body, said transfer system comprising a deformable and impervious wall positioned with respect to the recipient so that said wall forms a closed and sterile space inside which the orifice is located, a fluid communication device between the closed space and an outside of the recipient which can be handled without compromising sterility, and sealing means for the orifice, said sealing means being at least partially located inside the closed space so that the sealing means may be moved between an open position and a closed position of the orifice;
   creating communication between the first and second recipients by sterile handling of the fluid communication device;
   transferring the fluid from the first recipient to the body of the second recipient; and
   actuating the sealing means from an open position to a closed position by deformation of the wall.

17. The aseptic transfer process according to claim 16, further comprising establishing communication by a sterile connection between a first tube and a second tube that is divisible and is welded fitted onto the first recipient so that the communication is created with the fluid contained in said first recipient.

* * * * *